United States Patent [19]
Choi et al.

[11] Patent Number: 6,018,055
[45] Date of Patent: Jan. 25, 2000

[54] POLYARYLETHER CONTAINING N-SUBSTITUTED IMIDE GROUPS AND PROCESS FOR PRODUCING THE SAME

[75] Inventors: Kil-Yeong Choi; Dong-Hack Suh; Young-Taik Hong, all of Daejeon; Eun-Young Chung, Chungcheongnam-do, all of Rep. of Korea

[73] Assignee: Korea Research Institute of Chemical Technology, Daejeon, Rep. of Korea

[21] Appl. No.: 08/892,707

[22] Filed: Jul. 15, 1997

[30] Foreign Application Priority Data

Jul. 16, 1996 [KR] Rep. of Korea ................. 96 29570

[51] Int. Cl.[7] .................. C07D 487/02; C07D 487/04
[52] U.S. Cl. ............................................ 548/433
[58] Field of Search .................................. 548/433

[56] References Cited

FOREIGN PATENT DOCUMENTS

| | | |
|---|---|---|
| 5-117274 | 5/1993 | Japan . |
| 5-127405 | 5/1993 | Japan . |
| 5-142812 | 6/1993 | Japan . |

OTHER PUBLICATIONS

English–language translation (35 pages) of Japanese patent document (Kokai) No. 5–127405.

*Primary Examiner*—Deborah C. Lambkin
*Assistant Examiner*—Jane C. Osowecki
*Attorney, Agent, or Firm*—Ladas & Parry

[57] ABSTRACT

A polyarylether of the formula (VIII)

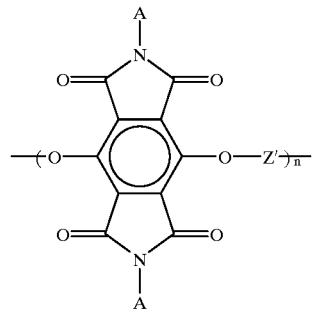

(VIII)

wherein wherein Z' is 1–3 optionally substituted rings selected from the group consisting of an aromatic ring, a hetero aromatic ring or an aliphatic ring.

A is —$R_1$—Z—Y in which $R_1$ is H, $C_1$–$C_{30}$-alkyl or -aralkyl or phenyl, Z is a direct bond or $CH_2$, S, O or NH, Y is $CH_3$, $OR_3$, $SR_3$, $NHR_3$, $N(R_3)_2$, $COOR_3$, COOM, $SO_3R_3$ or $SO_3M$ in which $R_3$ is $C_1$–$C_{30}$ alkyl and M is alkali metal, produced from 3,6-dihalogen- or -dintro-1,2,4,5-diimide having an N,N-substituent and which is suitable for use as a monomer for high temperature structural and functional polymers, and a process for producing the same are disclosed.

23 Claims, No Drawings

POLYARYLETHER CONTAINING N-SUBSTITUTED IMIDE GROUPS AND PROCESS FOR PRODUCING THE SAME

BACKGROUND OF THE INVENTION

1. Field of the Invention

The present invention relates to a novel polyarylether containing N-substituted imide groups and to a process for producing the same. More particularly, it relates to a polyarylether prepared by using a novel 3,6-dihalogen- or -dintro-1,2,4,5-diimide having N,N-substituents for use as monomers of high-temperature structures and functional polymers, and relates to a process for producing the same.

2. Background

Until recently, polyetherimide resin produced by General Electric in U.S.A. (Trademark: Ultem®) represented by the following formula (I) was known as a typical high-temperature engineering plastic:

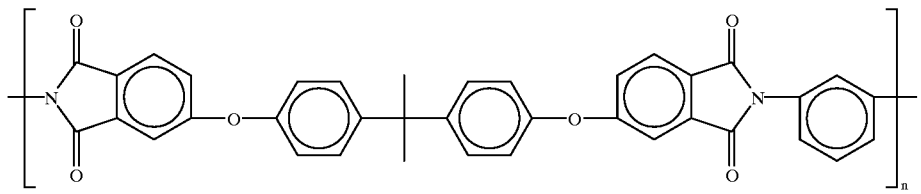

However, there is a demand to improve the processability and solubility of the engineering plastics.

SUMMARY OF THE INVENTION

It is an object of the present invention to provide a polyarylether containing N-substituted imide groups which render the polyarylether easy to introduce various functional groups by simple operations.

It is another object of the present invention to provide a process for producing a polyarylether containing N-substituted imide groups.

Other objects and advantages will be apparent to those who have ordinary skill in the art from the following description.

DETAILED DESCRIPTION OF THE INVENTION

The present invention relates to a polyarylether containing N-substituted imide groups, particularly to a polyarylether prepared by using a novel 3,6-dihalogen- or -dintro-1,2,4,5-diimide having N,N-substituents and to a process for producing the same.

The polymer of the present invention prepared by using a novel 3,6-dihalogen- or -dinitro-1,2,4,5-diimide having N,N-substituents is similar in its structural components, but quite different in its molecular structure, when compared to Ultem®. The thermal property of the polymer is similar to Ultem® (glass transition temperature: 218° C.), but has excellent processability and solubility. In particular, the polymer of the present invention is useful for synthesizing a functional polymer having a new property since various functional groups can be easily introduced to the substituent of 1,2,4,5-diimde having N,N-substituents by simple operations.

The present invention is described in detail below.

The present invention is directed to a 3,6-dihalogen- or -dinitro-1,2,4,5-diimide monomer having N,N-substituents represented by the formula (II)

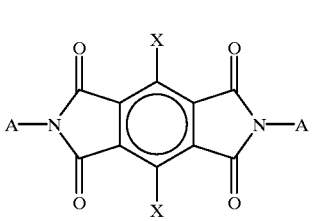

wherein A is —$R_1$—Z—Y in which $R_1$ is H, $C_1$–$C_{30}$-alkyl or -aralkyl, or phenyl, Z is direct bond or $CH_2$, S, O or NH, Y is $CH_3$, $OR_3$, $SR_3$, $NHR_3$, $N(R_3)_2$, $COOR_3$, COOM, $SO_3R_3$, or $SO_3M$ in which $R_3$ is $C_1$–$C_{30}$ alkyl and M is alkali metal, and X is halogen such as fluorine, chlorine or bromine, or a nitro group.

Further, the present invention is directed to a process for producing 3,6-dihalogen- or -dinitro-1,2,4,5-diimide derivatives having N,N-substituents which comprises reacting 1,2,4,5-tetramethylbenzene with a halogen compound (for example, fluorine, chlorine, bromine) or nitric acid to give 3,6-dihalogen or -dinitro-1,2,4,5-tetramethylbenzene of the formula (III)

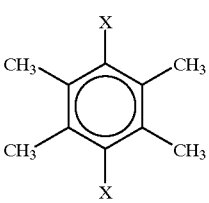

wherein X is as defined in the formula (II);

oxidizing the resulting compound by various oxidizing methods by using a transition metal catalyst, potassium permanganate or nitric acid to give 3,6-dihalogen- or -dintro-1,2,4,5-tetracarboxylic acid benzene of the formula (IV)

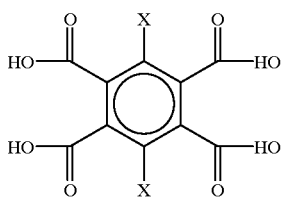

(IV)

wherein X is as defined in the formula (II);
reacting it with acetic acid or acetic anhydride to give 3,6-dihalogen- or -dinitro-1,2,4,5-tetracarboxylic anhydride of the formula (V)

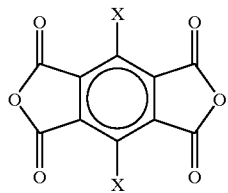

(V)

wherein X is as defined in the formula (II); and
reacting it with primary amine of the formula (VI)

$$NH_2—A \qquad (VI)$$

wherein A is as defined in the formula (II), to give a compound of formula (II).

The process for producing a compound of formula (II) is described in greater detail in the following: 1,2,4,5-tetramethylbenzene and iodine were introduced into petroleum ether and then hydrogen bromide, hydrogen chloride, hydrogen fluoride or nitric acid was added thereto. The resulting solution was vigorously stirred at about 0 to about 40° C. for about 1 to about 24 hours and then the resulting precipitate was filtered to give a compound of formula (III). The compound of formula (III) was introduced in pyridine and water and the resulting solution was reacted at reflux temperature of about 40° C. for about 2 to about 24 hours. While the solution was hot, the solution was filtered and then pyridine was distilled under reduced pressure. To the remaining residue were added water and sodium hydroxide and the resulting mixture was heated to about 40 to about 100° C. After the addition of potassium permanganate and reaction for about 2 to about 24 hours, the mixture was acidized with about 5 N HCl aqueous solution. The distillation of solvent gave a compound of formula (IV). To this were added acetic acid and acetic anhydride and then the mixture was reacted at about 40° C. to reflux temperature for about 30 minutes to about 24 hours to give a compound of the formula (V). The compound of the formula (V) and primary amine of the formula (VI) were stirred at about 0 to about 60° C. in a solvent such as methylacetic amide (DMAC), dimethylformamide (DMF), dimethylsulfoxide (DMSO) or N-methyl-2-pyrrolidone (NMP) for about 30 minutes to about 10 hours. Thereafter, a monomer of the formula (II) was synthesized either by charging acetic anhydride and pyridine or by ii) charging toluene and then was refluxed for about 30 minutes to about 24 hours.

The present invention also relates to a polyarylether and a process for producing the same which comprises reacting the monomer of the formula (II), synthesized as mentioned above with diol of the formula HO—Z'—OH (VII) or mixed diol thereof to give a polyarylether having diimide group of the formula (VIII)

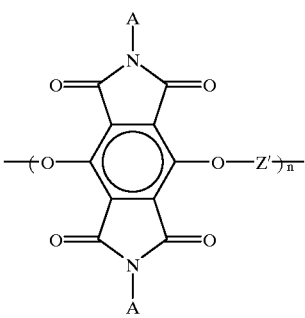

(VIII)

wherein Z' is at least one of an aromatic ring, at least one of a heteroaromatic ring, a cycloaliphatic ring, an aliphatic ring or a structure in which the above-mentioned rings are linked by a hetero atom,
n is an integer of 10 to 800, and
A is as defined in the formula II.

The typical example of diol of the formula (VII) is as follows:
bis-(hydroxyphenyl)-alkanes, bis-(hydroxyphenyl)-cycloalkanes, bis-(hydroxyphenyl)-ketones, bis-(hydroxyphenyl)-sulfones, bis-(hydroxyphenyl)-sulfoxides, α,α'-bis-(hydroxyphenyl)-diisopropyl benzenes and compounds having halogen groups at aromatic ring, for example 4,4'-dihydroxyphenyl, 2,2-bis-(hydroxyphenyl)-propane, 2,4-bis-(4-hydroxyphenyl)-2-methylbutane, 1,1-bis-(4-hydroxyphenyl)-cyclohexane, α,α'-bis-(4-hydroxyphenyl)-para-diisopropylbenzene, 2,2-bis-(3-methyl-4-hydroxyphenyl)-4-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-cyclohexane, α,α'-bis-(3,5-dimethyl-4-hydroxyphenyl)-para-diisopropylbenzene, 2,2-bis-(3,5-dichloro-4-hydroxyphenyl)propane and 2,2-bis-(3,5-dibromo-4-hydroxyphenyl)-propane.

The polymer of the formula (VIII) can be produced from a compound of the formula (I) and diol of the formula (VII) by 5 ways as described in the following.

3,6-dihalogen- or -dinitro-1,2,4,5-diimide having N,N-substituents of the formula (II) and i) a diol of the formula (VII) and an inorganic base compound, ii) a diol of the formula (VII), an inorganic base compound and a phase transfer catalyst, iii) a sodium salt or potassium salt of a diol of the formula (VII), iv) a sodium salt or potassium salt of a diol of the formula (VII) and a different phase transfer catalyst or v) a diol of the formula (VII) and an organic base compound are dissolved in dimethylsulfoxide, dimethylacetamide, N-methyl-2-pyrrolidone or dimethylformamide. The resulting solution is reacted at about 50 to about 200° C. for about 2 to about 72 hours and then precipitated in methylalcohol as a nonpolar organic solvent.

The molecular weight of the thus obtained polymer is determined by gel permeation chromatography. As eluent, polar solvent such as dimethylformamide, dimethylacetamide, dimethylsulfoxide or N-methyl-2-pyrrolidone is used. The molecular weight of the polymer is about 5,000 to about 300,000 g/mole, preferably about 10,000 to about 100,000 g/mole. In particular, a film is produced from a polymer having not less than about 20,000 g/mole of molecular weight. The glass transition temperature (Tg) measured by differential scanning calorimeter is about 100 to about 260° C. The thermal stability is measured by thermal gravity analysis. The polymer is thermally decomposed at about 330 to about 450° C. preferably about 350 to about 420° C.

The present invention will now be explained in more detail with reference to the following examples, but it is to be understood that the present invention is not restricted thereto and various modifications are possible within the scope of the invention.

EXAMPLE 1

0.5 mole of N,N-diphenyl-3,6-dichloro-1,2,4,5-diimide and 0.5 mole of bisphenol A were charged into 1 liter of dimethyl sulfoxide and then reacted at 180° C. for 24 hours while stirring under nitrogen atmosphere. In this case, no product was obtained.

EXAMPLE 2

0.5 mole of N,N-diphenyl-3,6-dichloro-1,2,4,5-diimide and 0.5 mole of bisphenol A disodium salt were charged into 1 liter of dimethyl acetamide and then reacted at 80° C. for 24 hours while stirring under a nitrogen atmosphere. The reaction mixture was cooled to room temperature and was subjected to precipitation by using methyl alcohol. The resulting precipitate was filtered and washed with methyl alcohol for several times. The precipitate was dried in a vacuum oven at 80° C. for 24 hours to give an orange product in a yield of 76%.

EXAMPLE 3

0.5 mole of N,N-diphenyl-3,6-dichloro-1,2,4,5-diimide and 0.5 mole of bisphenol A disodium salt were charged into 1 liter of dimethyl acetamide and then reacted at 160° C. for 24 hours while stirring under nitrogen atmosphere. The reaction mixture was cooled to room temperature and was subjected to precipitation by using methyl alcohol. The resulting precipitate was filtered and washed with methyl alcohol for several times. The precipitate was dried in a vacuum oven at 80° C. for 24 hours to give an orange product in a yield of 85%.

EXAMPLE 4

0.5 mole of N,N-diphenyl-3,6-dibromo-1,2,4,5-diimide and 0.5 mole of bisphenol A disodium salt were charged into 1 liter of dimethyl sulfoxide and then reacted at 80° C. for 24 hours while stirring under nitrogen atmosphere. The reaction mixture was cooled to room temperature and was subjected to precipitation by using methyl alcohol. The resulting precipitate was filtered and washed with methyl alcohol for several times. The precipitate was dried in a vacuum oven at 80° C. for 24 hours to give an orange product in a yield of 86%.

EXAMPLE 5

0.5 mole of N,N-diphenyl-3,6-difluoro-1,2,4,5-diimide and 0.5 mole of bisphenol A disodium salt were charged into 1 liter of dimethyl sulfoxide and 0.5 g of 18-crown-6 as a catalyst was added thereto. The reaction mixture was reacted at 180° C. for 24 hours while stirring under nitrogen atmosphere. The solution was cooled to room temperature and was subjected to precipitation by using methyl alcohol. The resulting precipitate was filtered and washed with methyl alcohol for several times. The precipitate was dried in a vacuum oven at 80° C. for 24 hours to give an orange product in a yield of 96%.

EXAMPLE 6

0.5 mole of N,N-dimethyl-3,6-dichloro-1,2,4,5-diimide and 0.5 mole of bisphenol A disodium salt were charged into 1 liter of dimethyl sulfoxide and 0.5 g of 18-crown-6 as a catalyst was added thereto. The reaction mixture was reacted at 180° C. for 24 hours while stirring under nitrogen atmosphere. The solution was cooled to room temperature and was subjected to precipitation by using methyl alcohol. The resulting precipitate was filtered and washed with methyl alcohol for several times. The precipitate was dried in a vacuum oven at 80° C. for 24 hours to give an orange product in a yield of 85%.

EXAMPLE 7

0.5 mole of N,N-diphenyl-3,6-dibromo-1,2,4,5-diimide and 0.5 mole of bisphenol A disodium salt were charged into 1 liter of dimethyl sulfoxide and 0.5 g of 18-crown-6 as a catalyst was added thereto. The reaction mixture was reacted at 180° C. for 24 hours while stirring under nitrogen atmosphere. The solution was cooled to room temperature and was subjected to precipitation by using methyl alcohol. The resulting precipitate was filtered and washed with methyl alcohol for several times. The precipitate was dried in a vacuum oven at 80° C. for 24 hours to give an orange product in a yield of 82%.

EXAMPLE 8

0.5 mole of N,N-diphenyl-3,6-dichloro-1,2,4,5-diimide, 0.5 mole of bisphenol A disodium salt and 0.1 mole of tetrabutylammonium chloride were charged into 1 liter of dimethyl sulfoxide and the reaction mixture was reacted at 160° C. for 24 hours while stirring under nitrogen atmosphere. The mixture wherein the reaction was completed was subjected to precipitation by using methyl alcohol and then filtered and washed with methyl alcohol for several times. The precipitate was dried in a vacuum oven at 80° C. for 24 hours to give an orange product in a yield of 90%.

EXAMPLE 9

0.5 mole of N,N-diphenyl-3,6difluoro-1,2,4,5-diimide, 0.5 mole of bisphenol A and 1.0 mole of isoquinoline were charged into 1 liter of dimethyl sulfoxide and then reacted at 180° C. for 24 hours while stirring under nitrogen atmosphere. The reaction mixture was subjected to precipitation by using methyl alcohol and then washed with methyl alcohol for several times. The precipitate was dried in a vacuum oven at 80° C. for 24 hours to give an orange product in a yield of 96%.

EXAMPLE 10

0.5 mole of N,N-diphenyl-3,6-dichloro-1,2,4,5-diimide, 0.5 mole of bisphenol A and 1.0 mole of isoquinoline were charged into 1 liter of dimethyl sulfoxide and then reacted at 180° C. for 24 hours while stirring under nitrogen atmosphere. The reaction mixture was subjected to precipitation by using methyl alcohol and then washed with methyl alcohol for several times. The precipitate was dried in a vacuum oven at 80° C. for 24 hours to give an orange product in a yield of 88%.

EXAMPLE 11

0.5 mole of N,N-diphenyl-3,6-dibromo-1,2,4,5-diimide, 0.5 mole of bisphenol A and 1.0 mole of isoquinoline were charged into 1 liter of dimethyl sulfoxide and then reacted at 180° C. for 24 hours while stirring under nitrogen atmosphere. The reaction mixture was subjected to precipitation by using methyl alcohol and then washed with methyl alcohol for several times. The precipitate was dried in a vacuum oven at 80° C. for 24 hours to give a brown product in a yield of 83%.

EXAMPLE 12

0.5 mole of N,N-diphenyl-3,6-dibromo-1,2,4,5-diimide, 0.5 mole of bisphenol A and 1.0 mole of pyridine were charged into 1 liter of dimethyl sulfoxide and then reacted at 120° C. for 24 hours while stirring under nitrogen atmosphere. The reaction mixture was subjected to precipitation by using methyl alcohol and then washed with methyl alcohol for several times. The precipitate was dried in a vacuum oven at 80° C. for 24 hours to give a brown product in a yield of 69%.

EXAMPLE 13

0.5 mole of N,N-diphenyl-3,6-dichloro-1,2,4,5-diimide, 0.5 mole of bisphenol A and 1.0 mole of potassium carbonate were charged into 1 liter of dimethyl sulfoxide and then reacted at 50° C. for 48 hours while stirring under nitrogen atmosphere. The reaction mixture was subjected to precipitation by using methyl alcohol and then washed with methyl alcohol for several times. The precipitate was dried in a vacuum oven at 80° C. for 24 hours to give a brown product in a yield of 58%.

TABLE 1

| Example | Product | Reactant | Reaction condition | Yield (%) |
|---|---|---|---|---|
| 1 | PDPIBA | DPDCDI<br>Bisphenol A | DMSO<br>180° C.<br>24 hour | |
| 2 | PDPIBA | DPDCDI<br>Bisphenol A disodium salt | DMAC<br>80° C.<br>24 hour | 76 |
| 3 | PDPIBA | DPDCDI<br>Bisphenol A disodium salt | DMAC<br>160° C.<br>24 hour | 85 |
| 4 | PDPIBA | DPDBDI<br>Bisphenol A disodium salt | DMSO<br>80° C.<br>24 hour | 86 |
| 5 | PDPIBA | DPDFDI<br>Bisphenol A disodium salt | DMSO<br>180° C.<br>24 hour | 96 |
| 6 | PDPIBA | 18-crown-6<br>DPDCDI<br>Bisphenol A disodium salt<br>18-crown-6 | DMSO<br>180° C.<br>24 hour | 85 |
| 7 | PDPI13A | DPDBDI<br>Bisphenol A disodium salt<br>18-crown-6 | DMSO<br>180° C.<br>24 hour | 82 |
| 8 | PDPIBA | DPDCDI<br>Bisphenol A disodium salt<br>Tetrabutylammonium chloride | DMSO<br>160° C.<br>24 hour | 90 |
| 9 | PDPIBA | DPDFDI<br>Bisphenol A<br>Isoquinoline | DMSO<br>180° C.<br>24 hour | 96 |
| 10 | PDPIBA | DPDCDI<br>Bisphenol A<br>Isoquinoline | DMSO<br>180° C.<br>24 hour | 88 |
| 11 | PDPIBA | DPDBDI<br>Bisphenol A<br>Isoquinoline | DMSO<br>180° C.<br>24 hour | 83 |
| 12 | PDPIBA | DPDBDI<br>Bisphenol A<br>Pyridine | DMSO<br>120° C.<br>24 hour | 69 |
| 13 | PDPIBA | DPDCDI<br>Bisphenol A<br>Potassium carhonate salt | DMSO<br>50° C.<br>48 hour | 58 |

PDPIBA: poly[(N,N-diphenyl-2,3,5,6-diimino)-1,4-phenylene-oxy-4-phenyleneisopropylidene-4-phenylene-oxy]
DPDFDI: N,N-diphenyl-3,6-difluoro-1,2,4,5-diimide
DPDCDI: N,N-diphenyl-3,6-dichloro-1,2,4,5-diimide
DPDBDI: N,N-diphenyl-3,6-dibromo-1,2,4,5-diimide

What is claimed is:
1. A polyarylether of formula (VIII)

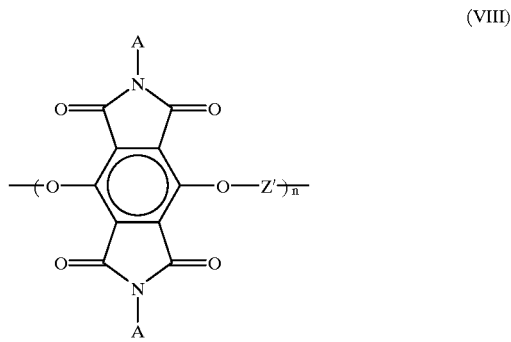

(VIII)

wherein the polyarylether is produced from a compound of formula (VII)

$$HO-Z'-OH \quad (VII)$$

and a compound represented by formula (II)

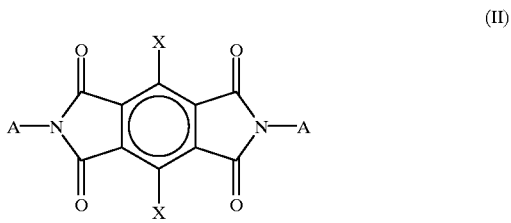

(II)

wherein $Z'$ is 1–3 optionally substituted rings selected from the group consisting of an aromatic ring, a hetero aromatic ring, and an aliphatic ring;
wherein A is $-R_1-Z-Y$ in which $R_1$ is H, $C_1$–$C_{30}$-alkyl or -aralkyl, or phenyl, wherein Z is a direct bond or $CH_2$, S, O or NH, wherein Y is $CH_3$, $OR_3$, $SR_3$, $NHR_3$, $N(R_3)_2$, $COOR_3$, COOM, $SO_3R_3$, or $SO_3M$ in which $R_3$ is $C_1$–$C_{30}$ alkyl and M is alkali metal;
wherein X is halogen or a nitro group; and
wherein n is an integer of 10 to 800.
2. A process for producing a polyarylether of formula (VIII)

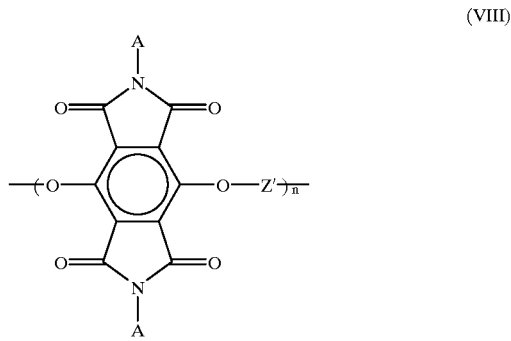

(VIII)

wherein A is $-R_1-Z-Y$ in which $R_1$ is H, $C_1$–$C_{30}$-alkyl or -aralkyl, or phenyl, Z is a direct bond or $CH_2$, S, O or NH, Y is $CH_3$, $OR_3$, $SR_3$, $NHR_3$, $N(R_3)_2$, $COOR_3$, COOM, $SO_3R_3$, or $SO_3M$ in which $R_3$ is $C_1$–$C_{30}$ alkyl and M is alkali metal, and Z' is 1–3 optionally substituted rings selected from the group consisting of an aromatic ring, a hetero aromatic ring, and an aliphatic ring, which process comprises i) reacting a compound represented by formula (II)

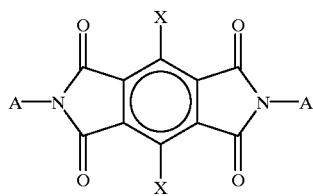

(II)

and a diol of formula (VII)

HO—Z'—OH (VII)

and an inorganic base compound; ii) reacting the compound of formula (II), a diol of the formula (VII), an inorganic base compound and a phase transfer catalyst; iii) reacting the compound of formula (II) and a sodium salt or potassium salt of a diol of the formula (VII); iv) reacting the compound of formula (II), a sodium salt or potassium salt of a diol of the formula (VII) and a phase transfer catalyst; or v) reacting the compound of formula (II), a diol of the formula (VII) and an organic base compound at about 50 to about 200° C. for about 2 to about 72 hours in an organic solvent to yield a solution containing the polyarylether of formula (VIII); and then precipitating the polyarylether of formula (VIII) by using a solvent.

3. A process as claimed in claim 2, wherein X is selected from the group consisting of fluorine, chlorine, and bromine.

4. A process as claimed in claim 2, wherein the compound of formula (II) is selected from the group consisting of N,N-diphenyl-3,6-difluoro-1,2,4,5-diimide, N,N-diphenyl-3,6-dichloro-1,2,4,5-diimide, and N,N-diphenyl-3,6-dibromo-1,2,4,5-diimide.

5. A polyarylether of the formula (VIII) as claimed in claim 1, wherein the compound of formula (VII) is selected from the group consisting of bis-(hydroxyphenyl)-alkane, bis-(hydroxyphenyl)-cycloalkane, bis-(hydroxyphenyl)-ketone, bis-(hydroxyphenyl)-sulfone, bis-(hydroxyphenyl)-sulfoxide, and α,α'-bis-(hydroxyphenyl)-diisopropyl benzene.

6. A polyarylether of the formula (VIII) as claimed in claim 1, wherein the compound of formula (VII) is selected from the group consisting of bisphenol A, 4,4'-dihydroxyphenyl, 2,2-bis-(hydroxyphenyl)-propane, 2,4-bis-(4-hydroxyphenyl)-2-methylbutane, 1,1-bis-(4-hydroxyphenyl)-cyclohexane, α,α'-bis-(4-hydroxyphenyl)-para-diisopropylbenzene, 2,2-bis-(3-methyl-4-hydroxyphenyl)-4-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-cyclohexane, α,α'-bis-(3,5-dimethyl-4-hydroxyphenyl)-para-diisopropylbenzene, 2,2-bis-(3,5-dichloro-4-hydroxyphenyl)propane, and 2,2-bis-(3,5-dibromo-4-hydroxyphenyl)-propane.

7. A polyarylether of the formula (VIII) as claimed in claim 1, wherein the polyarylether of the formula (VIII) is poly.

8. A process as claimed in claim 2, wherein the organic solvent is selected from the group consisting of dimethylsulfoxide, dimethylacetamide, N-methyl-2-pyrrolidone, and dimethylformamide.

9. A process as claimed in claim 2, wherein the solvent used to precipitate the polyarylether of formula (VIII) is methyl alcohol.

10. A process as claimed in claim 8, wherein the solvent used to precipitate the polyarylether of formula (VIII) is methyl alcohol.

11. A process as claimed in claim 2, wherein the diol of formula (VII) is selected from the group consisting of bis-(hydroxyphenyl)-alkane, bis-(hydroxyphenyl)-cycloalkane, bis-(hydroxyphenyl)-ketone, bis-(hydroxyphenyl)-sulfone, bis-(hydroxyphenyl)-sulfoxide, and α,α'-bis-(hydroxyphenyl)-diisopropyl benzene.

12. A process as claimed in claim 2, wherein the diol of formula (VII) is selected from the group consisting of bisphenol A, 4,4'-dihydroxyphenyl, 2,2-bis-(hydroxyphenyl)-propane, 2,4-bis-(4-hydroxyphenyl)-2-methylbutane, 1,1-bis-(4-hydroxyphenyl)-cyclohexane, α,α'-bis-(4-hydroxyphenyl)-para-diisopropylbenzene, 2,2-bis-(3-methyl-4-hydroxyphenyl)-4-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-cyclohexane, α,α'-bis-(3,5-dimethyl-4-hydroxyphenyl)-para-diisopropylbenzene, 2,2-bis-(3,5-dichloro-4-hydroxyphenyl)propane, and 2,2-bis-(3,5-dibromo-4-hydroxyphenyl)-propane.

13. A process as claimed in claim 8, wherein the diol of formula (VII) is selected from the group consisting of bis-(hydroxyphenyl)-alkanes, bis-(hydroxyphenyl)-cycloalkanes, bis-(hydroxyphenyl)-ketones, bis-(hydroxyphenyl)-sulfones, bis-(hydroxyphenyl)-sulfoxides, α,α'-bis-(hydroxyphenyl)-diisopropyl benzenes, bisphenol A, 4,4'-dihydroxyphenyl, 2,2-bis-(hydroxyphenyl)-propane, 2,4-bis-(4-hydroxyphenyl)-2-methylbutane, 1,1-bis-(4-hydroxyphenyl)-cyclohexane, α,α'-bis-(4-hydroxyphenyl)-para-diisopropylbenzene, 2,2-bis-(3-methyl-4-hydroxyphenyl)-4-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-cyclohexane, α,α'-bis-(3,5-dimethyl-4-hydroxyphenyl)-para-diisopropylbenzene, 2,2-bis-(3,5-dichloro-4-hydroxyphenyl)propane, and 2,2-bis-(3,5-dibromo-4-hydroxyphenyl)-propane.

14. A polyarylether of formula (VIII)

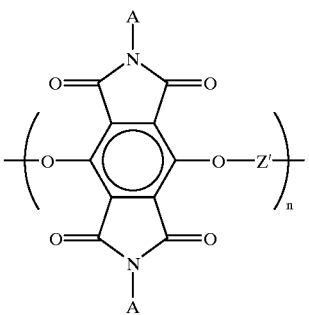

(VIII)

wherein Z' is 1–3 optionally substituted rings selected from the group consisting of an aromatic ring, a hetero aromatic ring, or an aliphatic ring, wherein A is —R$_1$—Z—Y in which R$_1$ is H, C$_1$–C$_{30}$-alkyl or -aralkyl, or phenyl, Z is a direct bond or CH$_2$, S, O or NH, Y is CH$_3$, OR$_3$, SR$_3$, NHR$_3$, N(R$_3$)$_2$, COOR$_3$, COOM, SO$_3$R$_3$, or SO$_3$M in which R$_3$ is C$_1$–C$_{30}$ alkyl and M is alkali metal, and n is an integer of 10 to 800.

15. A polyarylether of the formula (VIII) as claimed in claim 14 wherein Z' is selected from the group consisting of bis-(phenyl)-alkane, bis-(phenyl)-cycloalkane, bis-(phenyl)-ketone, bis-(phenyl)-sulfone, bis-(phenyl)-sulfoxide, and α,α'-bis-(phenyl)-diisopropyl benzene.

16. A polyarylether of the formula (VIII) as claimed in claim 14, wherein Z' is selected from the group consisting of phenyl, 2,2-bis-(phenyl)-propane, 2,4-bis-(phenyl)-2-methylbutane, 1,1-bis-(phenyl)-cyclohexane, α,α'-bis-(phenyl)-para-diisopropylbenzene, 2,2-bis-(3-methylphenyl)-4-propane, 2,2-bis-(3-chlorophenyl)-propane, bis-(3,5-dimethylphenyl)-methane, 2,2-bis-(3,5-dimethylphenyl)-propane, bis-(3,5-dimethylphenyl)-sulfone, 2,4-bis-(3,5-dimethylphenyl-2-methylbutane, 1,1-bis-(3,5-dimethylphenyl)-cyclohexane, α,α'-bis-(3,5-dimethylphenyl)-para-diisopropylbenzene, 2,2-bis-(3,5-dichlorophenyl)propane, and 2,2-bis-(3,5-dibromophenyl)-propane.

17. A polyarylether of the formula (VIII) as claimed in claim 14, wherein the polyarylether of the formula (VIII) is poly.

18. A process as claimed in claim 2, wherein Z' is selected from the group consisting of bis-(phenyl)-alkane, bis-(phenyl)-cycloalkane, bis-(phenyl)-ketone, bis-(phenyl)-sulfone, bis-(phenyl-sulfoxide, and (α, α'-bis-(phenyl)-diisopropyl benzene.

19. A process as claimed in claim 2, wherein Z' is selected from the group consisting of phenyl, 2,2-bis-(phenyl)-propane, 2,4-bis-(phenyl)-2-methylbutane, 1,1-bis-(phenyl)-cyclohexane, α, α'-bis-(phenyl)-para-diisopropylbenzene, 2,2-bis-(3-methylphenyl)-4-propane, 2,2-bis-(3-chlorophenyl)-propane, bis-(3,5-dimethylphenyl)-methane, 2,2-bis-(3,5-dimethylphenyl)-propane, bis-(3,5-dimethylphenyl)-sulfone, 2,4-bis-(3,5-dimethylphenyl)-2-methylbutane, 1,1-bis-(3,5-dimethylphenyl)-cyclohexane, α, α'-bis-(3,5-dimethylphenyl)-para-diisopropylbenzene, 2,2-bis-(3,5-dichlorophenyl) propane, and 2,2-bis-(3,5-dibromophenyl)-propane.

20. A process as claimed in claim 2, wherein the polyarylether of the formula (VIII) is poly[N,N-diphenyl-2,3,5,6-diimino)-1,4-phenylene-oxy-4-phenyleneisopropylidene-4-phenylene-oxy].

21. A polyarylether of the formula (VIII) as claimed in claim 1, wherein Z' is selected from the group consisting of bis-(phenyl)-alkane, bis-(phenyl)-cycloalkane, bis-(phenyl)-ketone, bis-(phenyl)-sulfone, bis-(phenyl)-sulfoxide, and α, α'-bis-(phenyl)-diisopropyl benzene.

22. A polyarylether of the formula (VIII) as claimed in claim 1, wherein Z' is selected from the group consisting of phenyl, 2,2-bis-(phenyl)-propane, 2,4-bis-(phenyl)-2-methylbutane, 1,1-bis-(phenyl)-cyclohexane, α, α'-bis-(phenyl)-para-diisopropylbenzene, 2,2-bis-(3-methylphenyl)-4-propane, 2,2-bis-(3-chlorophenyl)-propane, bis-(3,5-dimethylphenyl)-methane, 2,2-bis-(3,5-dimethylphenyl)-propane, bis-(3,5-dimethylphenyl)-sulfone, 2,4-bis-(3,5-dimethylphenyl)-2-methylbutane, 1,1-bis-(3,5-dimethylphenyl)-cyclohexane, α, α'-bis-(3,5-dimethylphenyl)-para-diisopropylbenzene, 2,2-bis-(3,5-dichlorophenyl)propane, and 2,2-bis-(3,5-dibromophenyl)-propane.

23. A polyarylether of the formula (VIII) as claimed in claim 1, wherein the polyarylether of the formula (VIII) is poly [(N,N-diphenyl-2,3,5,6-diimino)-1,4-phenylene-oxy-4-phenyleneisopropylidene-4-phenylene-oxy].

* * * * *